United States Patent [19]

Liprie

[11] Patent Number: 5,282,781
[45] Date of Patent: Feb. 1, 1994

[54] SOURCE WIRE FOR LOCALIZED RADIATION TREATMENT OF TUMORS

[75] Inventor: Sam F. Liprie, Lake Charles, La.

[73] Assignee: Omnitron International Inc., Houston, Tex.

[21] Appl. No.: 603,471

[22] Filed: Oct. 25, 1990

[51] Int. Cl.$^5$ ............................................. A61N 5/00
[52] U.S. Cl. ............................................ 600/3; 600/8
[58] Field of Search ................................... 600/1, 3, 6–8

[56] References Cited

U.S. PATENT DOCUMENTS 4,861,520  8/1989  van't Hooft et al. .................... 600/7

FOREIGN PATENT DOCUMENTS 0211066  7/1984  Fed. Rep. of Germany .......... 600/6

Primary Examiner—William E. Kamm
Assistant Examiner—John P. Lacyk
Attorney, Agent, or Firm—O'Connor, Cavanagh

[57] ABSTRACT

A composite source wire for use in treating malignant tumors within a patient's body by localized in vivo radiation with a radioactive source, via a catheter providing a path from a point external to the body to the tumor site. The source wire includes a thin continuous cylindrical flexible elongate stainless steel tube having encased therein a backbone wire running from its proximal end to a point short of its distal end to strengthen and enhance its flexibility, a cylindrical radioactive core adjacent to the distal end in abutting relation to the backbone wire, and a cylindrical plug at the distal end in abutting relation to the other end of the core, with the backbone wire, core and plug being tightly secured within the tube and the tube being securely enclosed about the plug with a tapered tip portion formed at that point. The source wire has an overall diameter sized to permit ease of movement through the catheter in advancement to the tumor site for the radiation treatment and to allow its retraction through the catheter from the point external to the body. The exterior surface of the tube is gold plated from its tip to the far end of the portion overlying the core. The source wire has an extremely small diameter (under 0.7 mm) and is sufficiently flexible that even in high radioactive dose sizes it is capable of passing through very narrow and even kinked catheters, making it useful for treating inoperable tumors such as common bile duct pancreatic cancer.

41 Claims, 2 Drawing Sheets

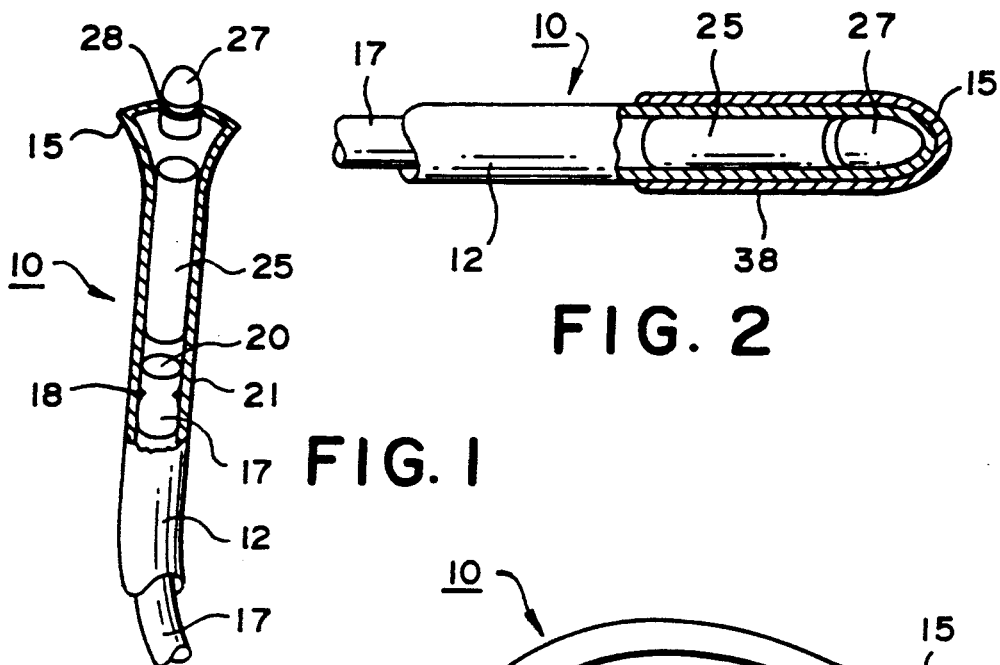
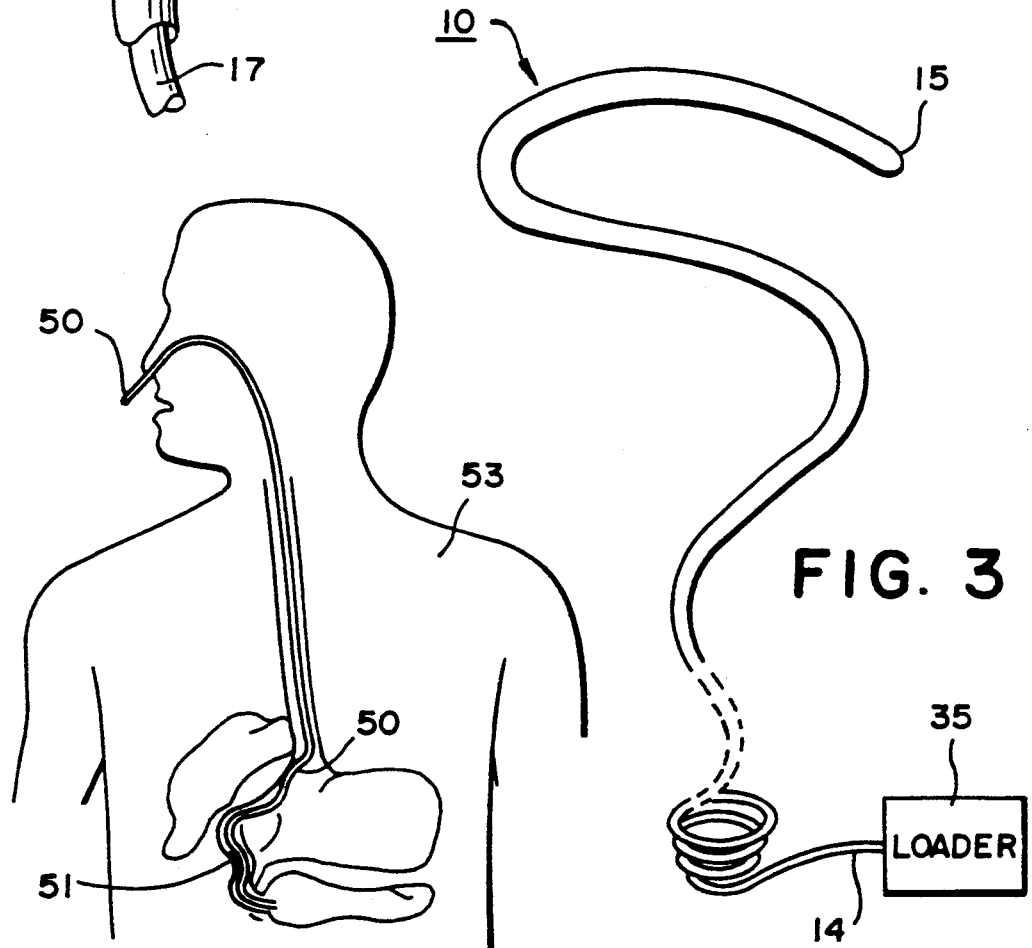

SOURCE WIRE FOR LOCALIZED RADIATION TREATMENT OF TUMORS

BACKGROUND OF THE INVENTION

The present invention relates generally to radioactive sources used in the treatment of cancerous tissue. More particularly, the invention resides in devices, apparatus, and processes for relatively short term delivery of a radioactive source into the body of a cancer patient to expose the malignant tumor(s) to localized in vivo radiation from within through a catheter which terminates at or beyond the tumor site.

Radiation treatment of malignant tumors is one of the three traditional methods of treating cancer, the other two being surgery and chemotherapy. One technique for radiation treatment involves directing a beam of radiation from a point external to the patient's body onto the area of the body in which the tumor is located. The purpose of such treatment is to shrink and ultimately destroy the tumor, but since the treatment is not particularly selective except in a very gross sense, in delivering the treatment healthy tissue is also exposed to the high dosage of radiation in the beam and is therefore subject to injury. Another technique for radiation treatment involves the delivery of a highly radioactive source into the body directly to the tumor site for localized irradiation, for the same purpose as the external beam radiation technique, except that in this treatment exposure and injury to healthy tissue can be avoided to a considerably greater extent than with the external beam radiation.

A conventional localized low level radiation procedure involves the use of radioactive sources or "seeds" having activity levels on the order of one millicurie per source or seed. Typically, the seeds are implanted in either of two ways. They may be injected directly into the tumor site after surgically opening the patient, the incision then sutured to close the patient, with the intention that the radioactive seeds will be left permanently in place.

A second technique is to implant one or more catheters in the patient's body to extend through the tumor site, then insert a tube containing the radioactive sources or seeds through one of the catheters into the region of the tumor where the tube is left in place for the predetermined period of treatment, and repeat the procedure for each of the other catheters. The low level seeds expose the tumor to gamma rays during the period they are left in place. While undergoing such treatment the patient remains ambulatory, but among the disadvantages of such procedures, in addition to the requirement of surgical implantation, the patient must remain in the hospital during the entire treatment phase which is usually several days, during which time all personnel working with the patient are exposed to radiation.

Another method of localized internal radiation treatment of deep tumors also involves implanting one or more catheters to provide a path from a point external to the patient's body to and through the tumor site, to provide accessibility to the interior of the tumor mass via the catheter(s). A highly radioactive source, typically having an intensity of ten curies, is then mechanically delivered on a retractable guidewire through the catheter for localized irradiation of the tumor for a very short period, usually in the range of only seconds up to a few minutes per treatment.

The high dose source is secured to the distal or remote end of the guidewire, and is advanced or retracted through an attachment of the proximal or near end of the guidewire to the loader machine, by appropriate manipulation of controls by the attending technician or physician from the control panel of a console for actuating the apparatus. The loader is located in a remote radiation shielded room into which the patient is moved for the treatment. The source wire is advanced through the catheter to the proper location for treatment of the tumor, based on measurement of the extent of advancement of a previously positioned dummy wire having an opaque tip marker for fluoroscopic observation. The dummy wire is retracted prior to moving the patient into the shielded room for the actual treatment.

In the case of an abdominal tumor, for example, an incision is made in the patient to open the abdominal cavity, and a needle is inserted into and through the tumor to provide a desired number of entries. A separate catheter is then implanted in each passageway formed by the needle, of sufficient length to be accessible from a point external to the body after the patient is closed. For purposes of determining or verifying the point to which the radioactive source wire must be advanced into the catheter for the treatment, a dummy wire is manually inserted into the catheter by the physician until the opaquely marked tip of the distal end is properly positioned as viewed under fluoroscope.

After this procedure is repeated for each catheter and the results are recorded, the patient is moved into the shielded treatment room, which is provided with apparatus to permit television viewing from outside, and the patient is hooked up to the loading machine. Using the controls on the console panel, the source wire is driven by the loader to the recorded (programmed) depth into the respective catheter, for example 100 cm. The source wire is left in place in that position for the time interval required for the treatment (which is also programmed into the loader). The source wire is then automatically retracted by the loader and returned to a shielded storage area within the loader.

If several catheters are implanted through the tumor site or region, the loader repeats the process automatically for each one. The source wire is driven into the first channel (catheter), the period of treatment is performed, the source wire is then withdrawn, a wheel on the loader turns automatically to the position for insertion of the source wire into the next channel, whereupon it is advanced through the new catheter to the proper depth and is retracted after the treatment interval, and so forth.

For treatments conducted on an outpatient basis, the catheters are left in place and the patient comes in for the procedure as scheduled. This is described in co-pending patent application Ser. No. 07/255,045, filed Oct. 7, 1988. Where the geometries of the catheters are fixed, as by the technique disclosed in that application, it is unnecessary to reimplant the catheters daily (or on other periodic bases, according to the treatment regimen), which serves to spare the patient from the considerable trauma of more surgery. This is particularly important for a patient experiencing life-threatening illness, and the resulting psychological effect. It is only necessary to verify by fluoroscopy that the catheters have not been dislodged, and if that is the case, a treatment card previously produced for that particular patient is simply inserted into the loader, to cause the loader to go through an automatic repetition of the treatment according to the prescribed regime.

The treatment regime may be repeated at regular short intervals over the entire period of time that the patient requires treatment to shrink and ultimately eliminate the tumor. Among the advantages of this type of radiation therapy are exposure of the tumor to fractionated treatment doses of localized radiation so that each individual treatment need only be of extremely short duration to provide the desired effect while reducing the magnitude of patient discomfort, and to provide more rapid shrinking of the tumor while avoiding prolonged exposure of healthy tissue to the radiation.

The loader has many additional functions but the foregoing description of its operation is sufficient for present purposes. In essence, the machine serves to move the highly radioactive source into the patient a precise distance for treatment of the cancerous mass, and then retracts the source. If the source wire encounters a kink or other barrier to its advancement along the catheter path, the feed mechanism of the loader is designed to slip, and upon detection of such slippage, to reverse the drive for retraction of the source wire into the shielded storage safe. An error flag is then displayed to the operator at the console panel, together with information that the source wire cannot be advanced into the particular catheter beyond the specified distance (at which the kink or other barrier was encountered).

Because the malignancy may be located deep within the body, and its nature and extent may make it inoperable, it may be extremely difficult to reach by use of the source wire as the latter is guided through the path provided by the implanted catheter. It may be necessary as a practical matter that the catheter take a long and tortuous route to the site of the cancer, with numerous sharp bends and turns as well as longer and narrower passages. It is essential, therefore, that the source wire should be extremely thin, small diameter and flexible, and yet sufficiently strong to traverse such a path and reach the cancer site without breakage or significant delay, and that it be retractable in the same fashion.

It is a principal object of the present invention to provide a new and improved radioactive source wire which possesses those desirable characteristics and features.

A feature of the present invention is the provision of a design which enables the source wire to be maneuvered through tight turns, even kinks, so that treatment may be rendered as scheduled without need for additional procedures to allow advancement to the tumor site.

One of the more serious problems encountered in the use of hot (radioactive) cores capable of delivering high dosage radiation to the tumor site by means of remotely activated electromechanical loader, is that the hot core is rigid and relatively brittle. A suitable core, for example, is composed of substantially pure iridium (although other conventional source materials such as cobalt, cesium, palladium, iodine and so forth may be used instead), which can be irradiated to a relatively high level of radioactivity in a rather small size. Ir-192, produced in a nuclear reactor with dosages of up to 10 curies in a diameter that results in a source wire diameter of about 1.1 millimeters (mm) is typical of the prior art. Unless the core is adequately protected and packaged it may scale, flake or even fracture when in use. The brittleness of the core tends to cause flaking during mere handling, which increases the order of difficulty of forming the source wire. If radioactive flakes are deposited on the wire or other surfaces in which the core comes into contact, the result is undesirable contamination.

Also, the method of attaching the core to the guidewire becomes critically important to assure its retention while the wire is being advanced into or withdrawn from the catheter, particularly in regions where binding may occur because of kinks and tight turns in the catheter. In one conventional prior art assembly the core is placed inside a stainless steel capsule with an open end on one side and welded to the delivery wire or guidewire. This technique suffers not only the disadvantage of increased flaking of the core material, but unless the weld is virtually perfect, can result in the presence of a dangerously weak spot at the point of the weld. Such weakness can result in fracture of the connection and separation of the core from the delivery wire in use, which would require emergency measures to be taken for its removal from the patient's body. Moreover, attempts to reduce the source and wire size, by reducing the respective outside diameter, only result in a decrease of the surface area to be welded, thereby further weakening the weld location.

A further object of the present invention is to provide a source wire for in vivo localized radioactive treatment of malignant tumors, in which the source wire components require no critical welds for their retention in the wire.

The rigidity of the typical hot core exacerbates the relatively unyielding nature of prior art source wires to tight turns in the catheter as the source wire is advanced or withdrawn therethrough. Beyond the possibility of breakage of the source wire from binding in the catheter, the surrounding tissue at the point of the binding is exposed to the high dosage of radiation for the duration of the time interval required to free the source wire, and the source wire may be prevented from being advanced fully to the tumor site.

Another object of the present invention is to provide an improved source wire which avoids such difficulties.

In my copending U.S. patent application Ser. No. 07/228,400, filed Aug. 4, 1988, there is disclosed a method of producing an ultra-thin iridium source wire of less than about 0.6 to 0.7 mm in diameter, by imbedding a smaller diameter core of substantially pure iridium in a hole drilled (e.g., by use of a laser) in a platinum wire of somewhat larger diameter than is ultimately desired, and then drawing the wire down to the smaller sized diameter. The platinum wire is reasonably strong and flexible, and despite the rigidity of the iridium core is capable of being maneuvered over relatively long passages through an implanted catheter, using a remote afterloader equipment.

After assembly, the overall substantially unitary source wire of the 228,400 application is irradiated in a nuclear reactor to provide the iridium core with the desired high dosage of radiation (depending on size of the iridium core) appropriate for delivery to the tumor site within the body. The small diameter of this source wire allows the use of a commensurately small diameter catheter. A preferred embodiment of that source wire system is a substantially pure iridium fiber core approximately one cm in length and about 0.2 mm diameter, disposed one mm from the distal end of the platinum delivery wire which is about two meters long. In practice, this source wire is advanced, positioned and retracted using a remote afterloader of the type disclosed in copending U.S. application Ser. No. 255,044, filed Oct. 7, 1988 in the names of Spako et al. and titled "Apparatus and Method for the Remote Treatment of Cancer Using High Radioactivity Sources."

Despite the important advantages of such apparatus and methods for in-vivo radiotherapy of malignant tumors, there are certain problems which remain to be addressed and resolved. A problem encountered with a highly radioactive core (high dose) source wire employing the principles of the invention disclosed in the 228,400 application is that the platinum becomes radioactive and is unusable for a period of several weeks (approximately ten platinum half-lives). In the meantime, the radioactivity of the core partially leaks away. The platinum wire and the cold iridium core imbedded in it are irradiated together in a nuclear reactor. The differential in the half-lives of the irradiated iridium and the irradiated platinum is important to the capability of the completed source wire to perform properly, but while the radioactive core becomes heavily radioactive, the platinum wire becomes slightly radioactive over a period of time and causes undesirable contamination.

It is another important object of the present invention to provide an improved design and method of fabrication for a high dose source wire.

A low dosage, hand loaded source wire having a platinum wire and iridium core is useful, because the cold core is readily encapsulated in platinum in long length on a spool, and the entire spool of wire may then be irradiated in a reactor. However, this source wire is of such low dose (typically, 0.4 to 25 milligram radium equivalent per cm, a standard unit of measure for radioactive strength) that the platinum contamination is insignificant. It is when the dosage exceeds one curie that the platinum contamination can become significant. In the low dose version, platinum is non-corrosive and will not oxidize in the presence of the radioactive core. The wire may be unspooled, cut into the length desired for treatment, and is self-sealing, as described in my copending patent application Ser. No. 07/061,468, filed Jun. 15, 1987.

It is a further object of the present invention to provide a low dose radioactive source wire having an improved design and method of fabrication, and which is readily usable in conjunction with a miniaturized source loader apparatus, or mini-loader, of the type previously described herein.

Yet another broad object of the present invention is to provide improvements in radioactive source wires and methods of manufacture thereof, to overcome the disadvantages found in prior art source wires.

SUMMARY OF THE INVENTION

According to one important aspect of the present invention, a new and improved source wire is provided for use in treating malignant tumors within a patient's body by localized in vivo radiation thereof with a radioactive source via a catheter providing a path from a point external to the body to the tumor site. The new source wire is extremely thin and flexible without sacrificing (and, in fact, while enhancing) the strength and reliability of device.

The improvement includes a generally cylindrical flexible elongate tube; a backbone wire encased within the tube from its proximal end to a point short of its distal end to enhance the flexibility of the tube; a generally cylindrical radioactive source or core encased and secured within the tube adjacent to its distal end in abutting relation at one end to the backbone wire; a generally cylindrical plug encased within the tube at its distal end in abutting relation to the other end of the radioactive source; the distal end of the tube being securely enclosed about the end of the plug opposite to the end thereof in abutting relation to the radioactive source, to form a tip portion. The composite source wire includes the tube and the backbone wire, radioactive source and plug encased therein, and has an overall diameter sized to permit movement thereof longitudinally through the catheter, whereby the source may be advanced into the catheter to the tumor site for radiation treatment of the tumor and thereafter withdrawn through the catheter, from the aforementioned point external to the body.

According to a feature of this aspect of the invention, the tube, which is composed of metal, preferably stainless steel, has an exterior surface which is gold plated throughout its length between the ends of the radioactive source encased therein. In a preferred embodiment, the gold plating extends over the tip portion of the tube to preclude oxidation of the plated surface and to improve the sealing of the tip.

According to another feature of this aspect of the invention, the radioactive source is secured in the tube substantially solely by the pressure exerted by the tube on the source, as a consequence of the crimping and drawing down of the tube, and the captive position of the source between the backbone wire and the plug.

In two high dose embodiments of the source wire, the source wire has a diameter of less than approximately 0.7 millimeters in one case and less than about 0.020 inch in the other, and the source itself is iridium irradiated to a level of at least approximately one curie, and preferably up to about 10 curies before being encased in the outer tube. In a low dose embodiment of the source wire, the source is an iridium fiber irradiated to a level of up to approximately one curie, and preferably in the range from approximately 200 millicuries to about one curie, and nominally about 500 millicuries.

According to this aspect of the invention, a process for manufacturing such a composite radioactive source wire includes the steps of providing a thin elongate metal tube having an outer diameter suitable for passage through a catheter to the tumor site, inserting a backbone wire having a diameter slightly less than the inner diameter of the tube into the tube to run from substantially its proximal end to a point short of its distal end, inserting a radioactive core having a diameter slightly less than the inner diameter of the tube into the tube from its distal end to abut against the end of the backbone wire, inserting a plug having a diameter slightly larger than the inner diameter of the tube into the tube from its distal end (this is accomplished by flaring a short length of the end of the tube to allow the plug to be placed) to abut against the other end of the core and substantially fill the remainder of the tube, and closing the distal end of the tube about the plug to form a seal at the tip and to secure the core in place within the tube. The distal end of the tube is flared at least slightly larger than and over a length about equal to the length of the plug to more readily accommodate the insertion of the radioactive core therein while reducing the possibility of flaking of the core material onto the exterior surface of the tube, and to accommodate the slightly larger diameter plug. Of course, this flaring is eliminated as a result of the final draw down of the tube and closure of the tip.

As part of the process of fabrication, the tube is crimped before draw down to secure the core in place therein. Subsequently, the tube is drawn down through a diamond die to a smaller outer diameter onto the backbone wire, radioactive core and plug remove air spaces between the interior surface of the tube and the core, backbone wire and plug, and to further secure those components in the tube. After the final draw down, the tip of the tube is gold plated over at least the portion of its length occupied by the core, and preferably over the entire tip.

In the process of fabricating a high dose embodiment of the source wire, the core is irradiated to a level of at least approximately 1 curie before insertion thereof into the tube, and the composite source wire comprising the tube, backbone wire, radioactive core and plug enclosed and secured therein is drawn down to an outer diameter of less than approximately 0.7 millimeters.

A high dose source wire fabricated according to that aspect of the present invention leads to another aspect of the invention, which is that the source wire is sufficiently thin, flexible and strong to allow it to be used for in vivo localized radiation treatment of pancreatic, liver, common bile duct and related cancers. Such treatment as that involving the common bile duct has not heretofore been possible using source wires which were available prior to those produced according to the present invention. This is primarily because the prior art source wires are not sufficiently flexible to make the bends and curves leading to the bile duct, and the is duct itself is much too narrow to be entered by the wire through a catheter implanted in that duct (and the source wire cannot readily be inserted through the duct alone without benefit of a catheter, because of problems with fouling the device). Source wires produced according to the present invention, however, have outer diameters less than 0.7 millimeters, and in one embodiment, approaching 0.018 inch, which can readily pass through the tight bends and the narrow catheter that must be implanted in the body leading eventually through the bile duct.

According to the invention, a method of treating pancreatic, liver, and related common bile duct cancers by in vivo localized radiation treatment, includes the steps of implanting a suitably sized catheter from a point external to the patient's body through the bile duct and into the area of the pancreas or other organ to be treated, advancing a composite source wire including a radioactive core (having a radioactive strength appropriate to treat the tumor) secured between a backbone wire and a plug within an outer tube catheter including the region of the bile duct and the area of the organ to expose the cancerous area thereof to radiation from the core for a predetermined time interval, and thereafter withdrawing the composite source wire from the catheter.

According to an aspect of this method of the invention, a closed tubular sheath of suitable size is inserted into and through the entire length of the catheter to be substantially coextensive therewith, before advancing the composite source wire through the catheter, to provide a protective sheath for the source wire during advancement, treatment and withdrawal. Also, advancement and withdrawal of the source wire into and from the catheter is performed using a remotely actuated loader to prevent exposure of the operator to radiation from the source wire.

According to another feature of the present invention, the tip portion of the composite source wire is tapered to ease the advancement of the source wire through the catheter. In one embodiment, the taper consists of a rounding of the plug and, thus, of the tip of the distal end of the tube which is closed over the plug, to form a bullet shape. In more elaborate embodiments, the tip of the source wire is implemented to provide a feeler structured to detect and open kinks and tight bends in the catheter along the path of the source wire to allow its passage therethrough without substantial binding.

In one of the latter embodiments, the source wire includes a tapered head having a relatively soft contoured tip, a segment of soft to medium hardness behind the tip, and a segment of medium to hard hardness behind the first-named segment, followed by a hard section of wire containing the core. In another embodiment, the tapered head of the source wire includes a series of balls, increasing in diameter from the tip backward thereof, secured on the tip for freedom of rotation in a plane normal to the axis of the source wire, except for the ball disposed at the tip which is fixed to form a contoured surface.

SUMMARY OF THE DRAWINGS

The above and still further objects, features and attendant advantages of the present invention will become apparent from consideration of the following detailed description of certain presently preferred embodiments and methods of the invention, taken in conjunction with the accompanying drawings, in which:

FIG. 1 is an exploded, partly cross-sectional and fragmentary view of a presently preferred embodiment of a composite source wire according to one aspect of the present invention;

FIG. 2 is a partly cross-sectional and fragmentary view of the assembled composite source wire of FIG. 1;

FIG. 3 is a perspective view, partly in phantom, of the source wire embodiment of FIG. 1 connected to an automatic source loader;

FIG. 4 is a partial view of the body of a patient illustrating the method in which the source wire embodiment of FIG. 1 is used in the treatment of pancreatic cancer, according to another aspect of the invention;

DETAILED DESCRIPTION OF THE PREFERRED EMBODIMENTS AND METHODS

Figure 5:
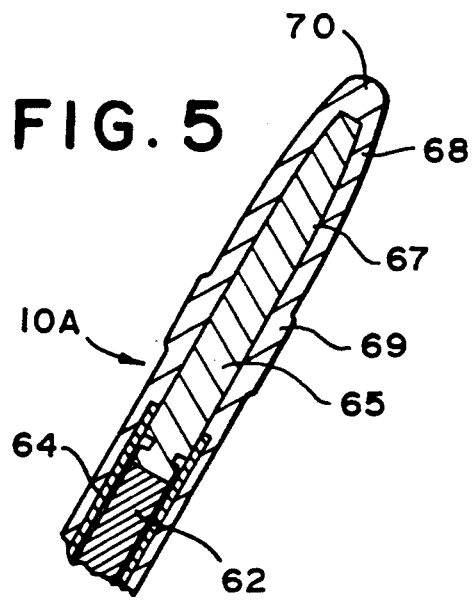
FIG. 5 is a cross-sectional view through the axis of a preferred embodiment of a symmetrical source wire having an improved tip portion according to still another aspect of the present invention.

Referring now to the drawings, and initially to FIGS. 1, 2 and 3, a composite source wire 10 according to the invention includes a number of components and elements. It is emphasized that the Figures of drawing are not intended to be to scale; for example, purely for the sake of greater clarity in the drawings, wall thickness and spacings are not dimensioned as they actually exist in the assembled embodiment. Among the components of the source wire 10 is a thin, continuous, elongate, flexible metal tube 12 having an outer diameter of about 0.7 mm or less, with a 0.58 mm outer diameter and a 0.1 mm wall thickness being optimum in the presently preferred embodiment, and a length adequate to reach the site of the tumor to be treated when the source wire is inserted through a catheter implanted in the patient's body for that purpose. Typically, tube 12 may have a length of 50 cm or more, for example.

Preferably, the tube is composed of stainless steel composition 316L, although other materials (such as titanium or tantalum) may alternatively be used. The critical aspects for the selection of the material for the tube include the following: The tube must be strong, flexible, non-corroding, capable of absorbing stresses to which it will be subjected, capable of blocking Beta radiation to assure treatment with only or substantially only Gamma radiation capability and ease of being plated, and capability to be drawn.

The tube has two ends, one of which will ultimately constitute the proximal end 14 and the other the distal end 15 of the composite source wire 10. The distal end of tube 12 is slightly flared outwardly, approximately 0.003 inch, and over about the last 3 mm of its length in the presently preferred embodiment (as best shown in FIG. 1) prior to assembly of the various components of the source wire, for a purpose which will be described presently.

Another component of the source wire is a backbone wire 17 which has a diameter slightly less than the inner diameter of tube 12 to allow it to slide easily therein, as the backbone wire is inserted to run virtually the entire length of the tube except for a portion at the distal end which is intended to accommodate two other components of the source wire. Backbone wire 17 is composed of extremely high tensile strength material, preferably stainless steel of the same composition as the tube, which may be a single strand or filament or a multi-strand cable.

One important purpose of backbone wire 17 is to substantially enhance the flexibility of the composite source wire 10. The outer tube 12 itself has a certain degree of flexibility, but in the absence of inner support could tend to bend or buckle, and therefore collapse, when undergoing tight turns through a catheter. That tendency is prevented by the presence of the internal backbone wire. In addition, the backbone wire acts as a safety wire. In the event that the outer tube were to rupture while being advanced or retracted through the catheter, the internal backbone wire will nevertheless retain the composite source wire together to permit its complete withdrawal from the patient's body.

After the backbone wire 17 has been inserted into the tube 12, air spaces between the two are removed to avoid oxidation of the separated surfaces. This is accomplished as follows. First, the backbone wire is pulled to extend slightly from the distal end (presently flared end) 15 of the tube, and crimp marks 18 are made in it adjacent to its end 20. Next, the backbone wire is pushed back into the tube so that its end 20 lies about 14 mm (in the construction of the presently preferred embodiment) from the end 15 of the tube. Then the tube is crimped at right angles at points 21 over the pre-crimped places on and along the backbone wire, to hold the latter temporarily in place within the tube. Finally, the assembled backbone wire and its tube sheath are drawn down through a smaller diameter diamond die, not beyond the point at which the tube overlies the backbone wire, up to about one-half inch of where the radioactive core will be inserted.

This creates a force fit between the tube and the backbone wire as the wall of the tube collapses tightly on the wire and bonds itself at each of the crimps. Any air space which existed between the surface of the backbone wire and the interior surface of the tube prior to the drawing down of the tube onto the backbone wire is now completely eliminated, or sufficiently so that there is virtually no opportunity for oxidation to occur within the tube at the two confronting cylindrical surfaces. Also, the external surface of the tube which forms the external surface of the composite source wire is completely smooth and burr-free, which is a considerable advantage in avoiding binding or catching of the source wire in the implanted catheter when in use.

In the fabrication of a high radioactive dose source wire (irradiated to a radioactive strength in the range from at least about 1 curie to approximately 10 curies, the actual level being at least adequate to treat the tumor), a "hot" source or core 25 consisting of a substantially pure iridium rod, which has been irradiated in a nuclear reactor to produce Ir-192 of the predetermined strength appropriate to its weight prior to assembly in the source wire, is inserted into the distal end 15 of tube 12. In the presently preferred embodiment of the high dose source wire, core 25 has a diameter of about 0.843 mm, a length of one cm (10 mm), and is irradiated to possess a radioactivity of up to about 10 curies (requiring an iridium core weight of approximately 21 milligrams for the 10 curie level) just prior to its assembly into the source wire.

The loading of radioactive core 25 into tube 12 presents a certain degree of difficulty because of brittleness of the hot core and consequent tendency to flake off and contaminate adjacent elements and fixtures. It is particularly important that the core be inserted with great care to avoid flaking of the core material onto the exterior surface of the tube. This is considerably aided by the presence of the slight flaring at the distal end 15 of the tube, which provides a "funnel" to better assure that the core enters the tube properly without scraping or flaking on the exterior surface of the tube. After the core 25 is inserted into tube 12 it continues inward until it abuts and is seated against the stop provided by the end 20 of the now tightly secured backbone wire 17 in the tube.

At this time, a metal plug 27, also preferably of 316L stainless steel, having a diameter slightly larger than the inner diameter of tube 12 (by about 0.0005 inch) is inserted into the flared end of the tube to abut and seat tightly against the free end of core 25. In the presently preferred embodiment of the composite source wire, plug 27 has a length of 8 mm (which is the reason for the same length of flared portion of the tube), is provided with an annular groove 28 approximately one mm wide and 0.001 to 0.002 inch deep located approximately one mm from its end which will reside closest to the hot core, and has a rounded or bullet shape at its other end which will reside at the tip of the distal end 15 of the source wire.

The annular groove serves to improve the crimping of the tube at that location onto the plug 27, which is done inwardly twice, the second at right angles to the first crimp. Thereby, the core 25 is temporarily secured in place, sandwiched between the ends of the backbone wire and the plug, and the plug is prevented from popping out during subsequent processing for completing the fabrication of the composite source wire. The crimping reduces the flare somewhat, but the end of the tube remains slightly flared. The plug may, if desired, be tack welded to the interior surface of the tube, not to maintain the plug in position after assembly, but simply to hold it temporarily during the crimping process.

The composite source wire 10 as thus far developed is then subjected to a final drawing down of the tube 12 through the diamond die. To assure the absence of residual flakes from the radioactive core, the exterior of the tube is wiped once before the final draw down. When the composite wire is drawn through a diamond die, the tube collapses in against the internal components to form a very tight force fit of the assembly. The plug 27, backbone wire 17 and core 25, which were held together when the outer tube 12 was crimped upon the plug, are now tightly secured together by the force exerted on them by the tube after draw down. The flared distal end 15 of the tube collapses tightly about the rounded end of the plug 27 to further maintain the assembly of the plug, the core and the backbone wire in place within the tube. As the tube wall collapses inward, it fills in to expel any air that might remain at the tube end, and causes the wall to attach itself to the plug with an extremely tight seal. The composite structure cannot then be easily disassembled, and the crimping at the grooves of the plug and the backbone wire assures an even tighter hold.

An alternative is to add a small amount (e.g., 0.5 mm thick) of silver solder (or other low melting point suitable noble material) at the end of the core before loading the plug into the tube, inserting the plug and then heating to a temperature sufficient to melt the silver to fill in all voids at its location completely, and thereby to form a secondary seal after crimping and draw down. The silver will not mix with iridium, as other materials may tend to do, and thus will preclude flaking of the iridium in the process of such secondary sealing.

As was noted earlier herein, prior art source wires have generally taught or recommended the use of welds between major components, to secure the components together. For example, in one widely used source wire the core is placed in an open-ended steel capsule and the open end is welded directly to a guidewire. The weld itself can constitute the strongest portion of the entire assembly (if only temporarily, because the radioactivity may tend to erode the weld over time), if it is done correctly. However, if the weld has any flaw whatsoever, it becomes the major weakness of the assembly and the most likely point at which breakage or rupture of the wire will occur. Also, even minor cracks in the capsule will result in leakage of core particles therethrough, resulting in dangerous radiation contamination.

The source wire of the present invention employs no welds in any location where strength of securing separate components is absolutely essential. That is, no welds are used between key components of the composite source wire. Indeed, the only places where welds may be used are for temporary attachments, such as for purposes of tacking two elements together to hold them in place as further assembly and final securing of the components is undertaken. In the source wire of the invention, the entire assembly is force fitted together within the outer metal tube, which is drawn down, preferably at least twice, through a diamond die.

As was also pointed out earlier herein, the internal backbone wire of the composite source wire is strong enough to resist breaking under virtually any commonly occurring circumstances of use. Therefore, if the tube 12 were to rupture in use for any reason whatsoever (which is highly unlikely), the strength of the backbone wire and the fact that it is force fitted into the outer tube by virtue of the crimps in and the drawing down of the tube, will nevertheless assure that the composite source wire can be fully retracted from the implanted catheter and into the loader 35 (FIG. 3).

The final draw down of the tube onto the plug, core and backbone wire encased therein also serves to eliminate virtually any remaining air spaces between confronting surfaces of those components at the interior of the tube 12. A key aspect of the source wire fabricated according to the method of the present invention is that the radioactivity emanating from the core will not seriously affect the interior surfaces or structure of the source wire, because the lack of air in the assembled unit will not allow undesirable reactions such as oxidation to take place.

Alternatively to providing the plug 27 with a rounded end before it is inserted into the end of the tube, so that when the tube is collapsed against the plug it assumes that shape at its tip, thin portions of the distal end 15 of the composite source wire 10 may be molecularly removed by conventional electroetching after the final draw down, to round off or taper the tip. Preferably, however, the rounding of the tip is achieved by arc welding. Unlike the prior art devices, this welding location is not intended for securing or attaching two components together, and provides only some additional sealing at the tip. The purpose of the rounded or tapered end of the composite source wire is to ease advancement of the source wire by the loader 35 through an implanted catheter to the tumor site for in vivo localized radiation treatment of the tumor. (Other embodiments of source wires designed to improve passage through kinks and tight curves in the catheter will be described presently.

At this point in the fabrication process, the exterior surface of the tip is preferably coated with a thin layer of gold by a conventional electroplating process. The composite source wire 10 is radioactive at its distal end 15, and is relatively well sealed at the tip. The gold plating may now be formed on the exterior surface of the tip, encompassing at least that portion of the surface overlying the length of radioactive core 25, and preferably extending over the entire tip portion as shown at 38 (FIG. 2) to about one half inch below the point at which the radioactive core is seated, back from the distal end of the tube, for purposes which will be explained presently. The gold plating cannot be applied earlier in the fabrication process because during draw down of tube 12 the diamond die would scrape the gold from the exterior surface of the tube.

The gold plating on the external surface of the tip of the composite source wire serves two important functions. Its principal function is to provide a non-oxidizing coating, and thereby prevent air from penetrating into the underlying metal surfaces of the assembly. In addition, this coating is not readily abraded or otherwise removed from the surface when the source wire is in use, either being advanced into or withdrawn from the catheter. Thus, it also provides an important sealing function. Despite the assembly technique in which the tube is crimped and drawn down over the backbone wire, and ultimately over the core and the plug, followed by the intentional collapsing of the slightly flared end of the tube over and tightly against the end of the plug, there remains a remote possibility that one or more tiny openings may exist between the end of the tube and the plug. The gold plating seals off any such leaks and tends to assure that no weak spots exist at the tip of the composite wire.

Although gold is preferred for this purpose, other non-oxidizing materials possessing the other desired characteristics may alternatively be employed.

This enhanced prevention of oxidation of the stainless steel tube from the high radiation level, and sealing of the tip of the tube against leakage of radioactive content, allows the wall thickness of the tube to be reduced to a thinness of approximately 0.1 mm, which enables further reduction of the diameter of the composite source wire.

All of the foregoing and any further assembly and fabrication process steps are conducted using either shielded hand manipulated or robotic techniques, in which the components, elements, fixtures and handling devices are located in a radiation shielded room remote from any human operator but visible through a viewing window. Preferably, the entire source wire fabrication process is conducted in a robotic laboratory unit, through the use of electromechanical control mechanisms which are actuated either by an automated computer process or by a human attendant at a console outside the shielded unit.

Unlike the high dose source wire described above, a mini-dose source wire for use with a mini-loader machine may be produced manually (using an otherwise virtually identical process to that described above) because of its relatively low dosage of radioactivity, but nevertheless requires assembly behind leaded glass and lead shields using hand manipulators so that the human assembler is not exposed to the radiation. In any event, such devices as forceps, diamond die, and anything that may touch the distal end of the source wire after the radioactive core is loaded must be decontaminated before another source wire may be fabricated.

A high dose 10 curie source wire employs a nominally one cm long hot core, which is extremely hard and brittle. A low dose, mini-dose or mini-loader composite source wire embodiment according to the present invention, on the other hand, may employ an iridium-192 fiber core having a diameter of approximately 0.005 inch, and consequently provides even greater flexibility than the high dose source wire. Experiments have shown that a mini-dose wire constructed according to the method of the invention may be wound in circles as tight as one-half inch diameter. It is fabricated by the same method as is described above for the high dose source wire, but with considerably smaller components, including tube, backbone wire (which may, for example, be music wire), core and plug.

For example, instead of a tube having a 0.0230 inch outer diameter as is used with the high dose wire, the miniloader wire stainless steel tube may have an outer diameter of 0.020 inch and an inner diameter of 0.010 inch, which substantially improves the flexibility of this low dose composite source wire over even that of the enhanced flexibility high dose wire described above. Because both the high dose and low dose wires of the present invention are fabricated identically except for sizes, all components are proportional. The wall thickness of the tube may be less with the low dose source wire, although a wall thickness of 0.004 inch appears to be ideal for both types in the presently preferred embodiments.

The radioactive core is custom fitted according to the size of the tumor to be treated, in that the fiber core of iridium is cut to size for the mini-dose source wire and inserted into the tube to abut against the music wire, a plug is inserted and the tube is crimped against it, and the composite structure is then drawn through a diamond die. The preferred embodiment of such a mini-loader wire can pass through a 21 gauge needle, whereas the high dose wire cannot pass through less than a 20 gauge needle.

The mini-dose source wire typically would not be charged to a level of radioactivity as great as the high dose wire because of the smaller quantity of iridium in the core. Rather, with the dimensions which have been described for the preferred embodiment of the mini-loader source wire, the core fiber may be irradiated to a dosage of, typically, in the range from about 200 millicuries to one curie, and nominally about 500 millicuries. (Depending on the length of the core —actually the amount of core material—it is possible to charge even such a small OD core to the 10 curie range, but because the length would be considerable and it is unlikely that a core length exceeding 10 centimeters would ever be required for treatment of a tumor, the maximum charge would more likely be in the range of 5.0 curies). Because of the typically lower dosage it is not essential, but is nevertheless desirable, that the tip of the composite mini-dose wire be gold plated.

Unlike the typical fixed length of 10 mm for high dose wires, as noted above, the core of the mini-dose wire may be cut to selected diverse lengths appropriate to the particular sizes of the tumors to be treated. A technique by which this may be easily accomplished is disclosed in my aforementioned co-pending U.S. patent application Ser. No. 07/061,468. For example, if a 5 cm and a 2 cm length core are available for use in treating a 6 cm tumor, the tumor can either be overtreated by using the 5 cm length, withdrawing it and then using the 2 cm length, or by using the 2 cm length core alone for 18 minutes (for example), withdrawing it slightly to the next segment to be treated, used for another minutes, withdrawn slightly again and used for another 18 minutes, thereby treating the entire 6 cm length of the tumor. Ideally, it is desirable to treat the tumor so that a safety zone is provided on both sides. i.e., so that the exposure to radiation extends beyond the sides. For example, for a 2 cm tumor, a 4 cm core may be optimal.

On the other hand, a high dose wire with a one cm core length may be employed to treat tumors of different sizes because of the high dosage of radiation it delivers. It is advanced to the treatment site and maintained in place there for only a matter of seconds, and then retracted in small steps (e.g., one cm steps) until the entire length of the tumor has been treated.

The mini-loader for driving the low dose source wire uses the same basic drive system as a high dose source wire loader. However, the high dose loader must be kept in and operated in a shielded room typically having a wall thickness including about one foot of concrete and at least 4 inches of lead shielding. The mini-loader can drive the radioactive source into the patient for treatment and retract the source afterward right in the doctor's office or at the patient's bedside in the hospital room.

To provide even greater thinness and flexibility of the high dose composite source wire, rather than using a one cm long hot core with a 0.0185 inch outer diameter, mounted inside the stainless steel tube 12 (FIGS. 1-3) for an overall source wire outside diameter of 0.0280 inch, as in the preferred embodiment of the high dose wire described above, an alternative embodiment employs a longer, thinner core. For example, a core having a two cm length (i.e., a doubling of that dimension from the preferred embodiment) would permit reduction of the diameter to permit the core to be irradiated to a radioactivity level of 10 curies, and to an extent that the diameter of the resulting composite source wire is on the order of approximately 0.018 inch. The result is a source wire of considerably enhanced flexibility. The essential element is that approximately 21 milligrams of substantially pure iridium must be used in the core in order to permit it to be irradiated to a level of about 10 curies.

Irradiation of the core to the desired (and possible) radioactive strength is performed typically by placing the iridium in a research reactor, which is generally capable of providing 550 curies per gram of iridium material. The material is maintained in a neutron flux and a determination is made of how many neutrons need to be activated and the length of time the material must be exposed to the calculated flux, for example 1,081 hours. By increasing the length of the core. It is possible that the irradiation to the desired dosage or strength may be performed within a shorter time interval, through the increased surface area.

The extremely thin, flexible and high strength high dose composite source wire produced according to the present invention provides a considerable advantage for treatment of certain particularly remotely located cancers. For example, in the case of liver cancer and/or pancreatic cancer or related organ cancers, in vivo localized radiation treatment from within the cancerous mass has not been possible using heretofore available source wires. For such treatment it is necessary for the radioactive source to reach and then pass through a catheter implanted in the biliary tract or bile duct, which is an extremely narrow passageway. Radioactive source wires produced by techniques taught by the prior art are too large and inflexible to pass through the duct, much less the even narrower passageway afforded by the catheter implanted therein.

In contrast, the present invention provides a source wire which is of sufficiently small diameter and enhanced flexibility, together with improved non-binding tip design, to be driven through the very tight curves and bends encountered along the tortuous path through which it must pass to reach the bile duct, and then through the duct itself (or the implanted catheter). This is essential in order to enter the regions in which the pancreatic cancer, liver cancer or related cancer may be exposed to the localized radiation from within the tumor mass.

As a practical matter, such cancers generally are inoperable, because the disease has usually metastasized to reach that location and is in its advanced stages. At that point, the treatment is limited primarily to attempts to relieve the patient's pain and discomfort during the remaining few months of survival. External beam radiation, implanting of radioactive seeds (in which the patient is opened up and small seeds are shot into the pancreas, for example), chemotherapy and surgery have proved unsuccessful on these types of cancers other than to keep the patient alive for a relatively very short period after discovery and initiating treatment of the cancer It is not even clear that the nature of the treatment of this type of cancer to date may not contribute to earlier demise of the patient than would have occurred had no treatment been rendered. The radiation treatment permitted according to the present invention offers the possibility of a longer period of patient survival, and perhaps even cure because it can be conducted at and from within the tumor site to produce shrinkage and even potential elimination of the cancer.

Referring to FIG. 4, the method of using the high dose composite source wire according to the present invention for treating pancreatic cancer and related organ cancers is as follows. First, a 10-French catheter (a standard type of nasal-biliary drainage set) 50, which is the largest tube that can be inserted into the bile duct is implanted into that duct 51 commencing from the nasal passage of the patient 53. Even the use of this small sized catheter is limited to situations in which there is no significant constriction of the duct. Actually, the catheter is inserted through the nasal passage and allows a shunt to be placed in the bile duct. The shunt catheter passes through the patient's esophagus, stomach and the bile duct, from which it may reach the pancreas and the liver. The catheter must wind through this tortuous path which consists of many tight curves as well as some straight passages and terminates at or beyond the very tiny opening provided by the bile duct.

The 10-French nasal biliary drainage set must be pushed through a constricted bile duct, and the shunt can be advanced all the way into the pancreas. The catheter tube is provided with holes to allow drainage of bile through a connection at one end to a suction pump. The set also allows the attending physician or technician to view the condition of the organ at the other end. It Is conventionally used to clean out bile, for aspiration and pain relief and related purposes, but is not employed for purposes of effecting a cure or any treatment which could lead to cure of a tumor. The ultra-thin flexible high dose source wire of the present invention, however, can be advanced by the source loader through the drainage set and the shunt tube into the bile duct to treat the pancreatic or related tumor from within the mass. The source wire is maintained in place for the time interval prescribed by the oncologist, and is then retracted back into the loader.

The principal limitation of external beam radiation is that only a certain level of radiotherapy can be delivered because of the many sensitive and critical organs in the vicinity which would be damaged or destroyed by excessive levels of radiation. However, by providing the radiation treatment directly inside the cancerous area of the pancreas, the surrounding sensitive and healthy organs are spared from excessive levels of radioactivity while the cancer receives a heavy dosage. Not only can this method provide a desirable palliative treatment in the worst cases, but the possibility of a cure exists depending on the nature and extent of the cancer in the area.

Because of the presence of bile in the duct it is imperative that the source wire not be introduced directly into the duct or exposed to direct contact with the bile, which can cause numerous problems of contamination, loss of optical sensors within the afterloading equipment, and the like. The preferred embodiment of a high dose composite source wire according to the invention is sufficiently small and flexible to use additional conventional tubing with a closed end and an opaque marker (observable under fluoroscopy), as a protective sheath for the source wire. Initially, a dummy guidewire is fed into the protective sheath to introduce and advance it into the catheter as the guidewire itself is advanced. The movement is guided under fluoroscope until the guidewire and overlying sheath are lined up in the bile duct. Then the guidewire is removed, leaving the sheath in place.

The patient is then moved to the shielded radiation treatment room and the catheter tube is hooked up to a source loader. The high dose source wire is then driven through the catheter (via the internal protective sheath) and advanced through the bile duct to the point at which the dummy wire was advanced, according to the measured distance of travel from the open end of the catheter to the point of placement of the tip of the dummy wire in the pancreas. The cancer is then treated by exposure to a high dose of radiation from the region of incidence of the cancer by leaving the source wire in place for the prescribed few seconds required, retracting in small steps (typically, one cm) until the entire treatment is rendered, after which the source wire is fully retracted by the loader. The protective sheath is then readily removed from the catheter and disposed of. In this way the source wire remains in a clean and reusable condition following its use in treatment. The source wire is sufficiently small that it will be accommodated by the internal sheath inside the smallest inner diameter tube that can be accommodated by the bile duct.

The protective sheath may be composed of any biocompatible material, such as teflon or polyethylene, and be provided with its own solid stylet backbone wire which is used as the guidewire to advance it into the catheter and position it properly. As noted above, the guidewire is then removed. It is preferred that the sheath not be introduced and advanced into and through the catheter together with the source wire, because by positioning the sheath first it may be readily determined to be properly positioned, and also because it can then be determined how far the source wire must be advanced into the catheter, from the position of the opaque marker at the end of the sheath.

Referring now to FIG. 5, a preferred embodiment of a composite source wire 10A having an improved tip portion (relative to the simple rounded or bullet shape taper of the preferred embodiment described earlier herein) according to an aspect of the invention is shown in cross-section therein. The composite source wire may be and preferably is fabricated in the same way as has been described above for the preferred embodiment of the high dose source wire, except as will be explained below. Only a portion of the radioactive core 62 is shown in FIG. 5, encased within stainless steel tube 64 and abutting at one end against the backbone wire (not shown).

A plug filament 65 of stainless steel, preferably having a length of one cm, a nominal diameter of 0.015 inch and slightly tapered at one end, is inserted at the other end into the tube 64 (aided by the flaring of the tube) to an extent of 3 mm to abut against the core and extend outwardly from the end of the tube by about 7 mm. The plug has an annular groove adjacent its end seated against the core, for the same purpose as was described above for the preferred high dose wire embodiment, i.e., for ease of crimping the tube inwardly against the plug and thereby to hold the components in place prior to drawing down the tube. After the tube is drawn down, the exposed partially tapered end of the plug filament 65 extending from the tube and a portion of the exterior surface of the distal end of the tube down slightly past the length of the tube occupied by core 62 are plated with an ultra-thin layer 67 of gold, approximately 0.0001 to 0.0005 inch thick. This layer provides a non-oxidizing surface and seals any tiny openings that may exist between the end of the tube and the plug filament after the drawing down of the tube.

The entire exterior surface of the tube from a point slightly below the core and of the plug filament (including the gold plating thereon) is then coated with a layer 68 of permanent bonding material, preferably a commercially available material known as Techoflex (produced by Thermedics Inc. of Woburn, Mass). This material is flexible when cured, and returns to its original shape after being deformed. The Techoflex layer 68 is resistant to radiation in that its composition is not affected as would cause it to become brittle or otherwise deteriorate, and the material is also strong and sufficiently slippery or slick that it tends to reduce friction and binding between the tip of the source wire and the inside surface of the catheter in which the source wire is being advanced. The Techoflex coating is preferably also tapered down over the back portion of the tube 64 just below the end of core 62 (not shown) that abuts the backbone wire, to allow the source wire to be withdrawn readily from the catheter as well. Layer 68 is formed on the surface of the plug 65 to provide a somewhat more gradual and longer taper terminating in a short length 69 of larger diameter than the rest of the source wire.

The very tip 70 of this overall feeler tip assembly portion of the composite source wire 10A is rounded to offer little resistance as the source wire is ultimately advanced in the catheter. Tip 70 provides a relatively soft, flexible and rounded surface, whereas the tapered section of plug 65 with its tapered overlying layer 68 provides a soft to a medium hardness segment. In further contrast, the non-tapered segment of the plug and the larger diameter portion 69 of layer 68 and extending down to the distal end of tube 64 provide a medium to hard hardness segment.

Figure 7:
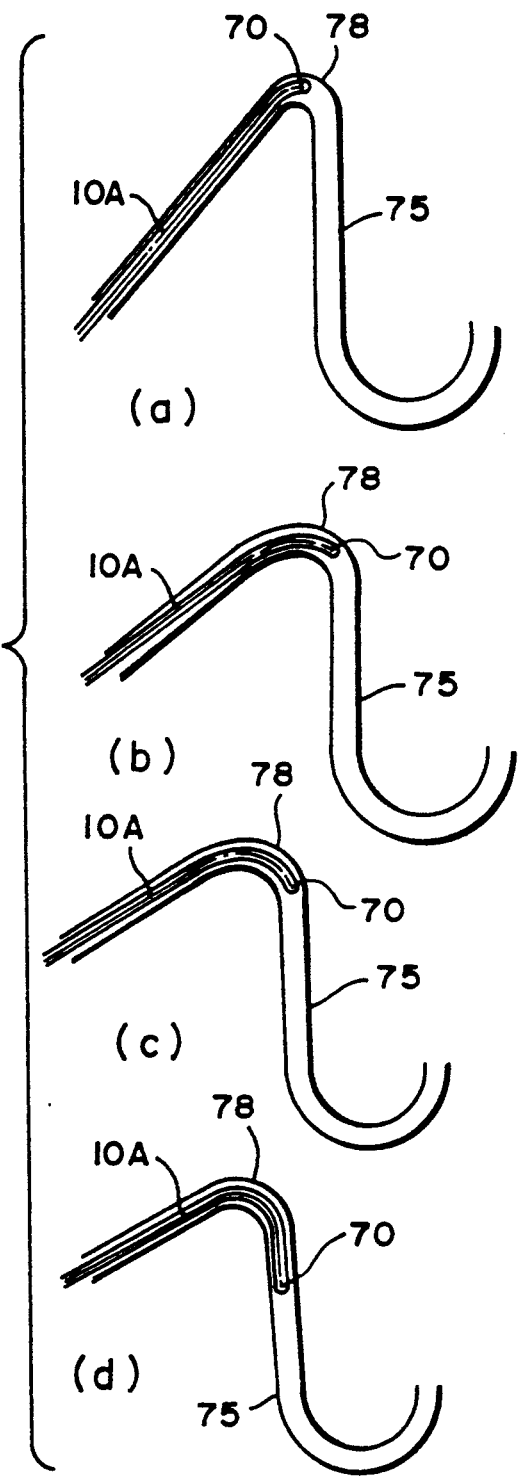
FIGS. 7(a), (b), (c) and (d) illustrate the sequence of advancement of a source wire embodiment of either of FIG. 5 or 6 through a relatively tight curve in the catheter.

With these characteristics of soft to medium to hard segments of the source wire extending back from tip 70, and the extreme flexibility of the underlying plug filament, the feeler tip assembly portion serves to enhance the passage of the source wire through tight curves or kinks in the catheter as will be appreciated by reference to the sequence of schematic diagrams of FIGS. 7(a), (b), (c) and (d). In FIG. 7(a), the source wire 10 is being advanced through the implanted catheter toward a tight bend therein. The feeler tip portion 70 is just entering the sharp angle 78 of the bend.

The soft and most flexible rounded segment of the tip portion 70 of the source wire enters the sharp angle 78, and the soft to medium segment following it tends to begin straightening the angle as shown in FIG. 7(b). As the soft to medium segment of the tip portion moves further into the angle 78 (FIGS. 7(b) and (c)), it further opens the angle to a more graceful curve, effectively straightening (although not fully, of course) that section of catheter 75. This is caused primarily by the relative hardness (i.e., soft to medium) of that segment. Also, the flexible taper ending in the larger diameter segment 69 of the improved tip portion of the source wire is of sufficiently large diameter that it tends to expand the catheter at the tight bends or sharp curves in the catheter as the source wire is advanced through those bends.

This assists in straightening the whole kinked portion and causing it to distort. Finally, in FIG. 7(d), the tip 70 of composite source wire 10A has advanced through and beyond the sharp angle section 78.

This performance of the source wire in advancement through the catheter is a considerable improvement over the typical performance of prior art radiotherapy source wires, which have exhibited a propensity to bind and stop, or break, when such an angle or curve is encountered. The improved tip portion of this aspect of the present invention also provides improved performance as the source wire is retracted after radiation treatment, because of the slightly tapered portion of layer 68 below the core.

Figure 6:
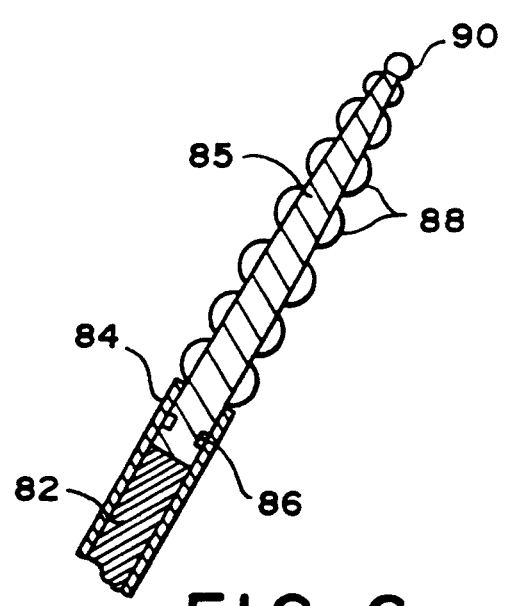
FIG. 6 is a cross-sectional view of another embodiment of a symmetrical source wire with a improved tip portion according to the invention.

An alternative embodiment of the improved tip portion of the source wire is shown in FIG. 6. The backbone wire (not shown), core 82 and plug filament 85 are composed of the same materials and assembled in the same way as described for the previous embodiments, except that here, as in the case of the embodiment of FIG. 5, plug filament 85 preferably has a length of one om and is inserted into the tube 84 to the extent of 3 mm of that length. The tube is then crimped inwardly at the annular groove 86 in the plug filament to hold the filament in place, and the latter extends outwardly at the distal end of tube 84 by about 7 mm.

Here also, after the tube is drawn down over the internal components, the surface of the plug and at least the portion of the exterior surface of the tube extending past the length occupied by the core are covered with a very thin gold plating. In this embodiment, a Techoflex layer need not be applied to the exterior surface of the tube as was done in the embodiment of FIG. 5, and would not be used over any portion of the plug filament.

Thereafter, eight or nine balls 88, each having an appropriately sized hole drilled through its center are loaded in a stack onto the exposed end of plug filament 85. The plug constitutes a solid filament having a 0.014 inch diameter in the preferred embodiment of this alternative, and each of the balls 88 in the stack has a hole size of 0.015 inch. The smallest ball 90 at the top of the stack (the tip of the feeler assembly portion of the composite source wire) has a 0.019 inch diameter and is tack welded to the tip of the plug to hold all of the other balls stack ed and free to move slightly along the axis of the plug and to rotate in planes normal to that axis.

The plug is substantially the same diameter throughout, but a taper is provided from narrow to larger (and then slightly reduced proportions) backward from the tip because of the size and position of the balls stacked on the plug. As noted above, in this preferred embodiment of a feeler tip assembly ball 90 at the tip has a 0.019 inch diameter. The next three balls have diameters of 0.020, 0.022 and 0.023 inch, respectively, starting from the closest to ball 90, and one or two balls closest to the distal end of tube 84 each has a diameter of 0.023 inch. Each of the remaining two or three balls between those two sets has a 0.024 inch diameter, to provide the widest diameter portion of the feeler tip assembly. Sufficient space is provided between the balls to allow them to slide back and forth slightly, which is important to allow the feeler tip assembly to self adjust itself as it moves ahead of the rest of the composite source wire through bends, curves and kinks in the catheter as the source wire is advanced to the tumor site.

As with the embodiment of FIG. 5, the feeler tip assembly of FIG. 6 allows the composite source wire to be maneuvered through kinks and sharp bends or curves in the catheter during advancement to the tumor site. Here, the stack of balls on the plug filament provides the taper ending in the largest diameter balls, which are of sufficiently large diameter to tend to expand the catheter at the tight bends or sharp curves therein as the source wire is advanced through those bends. As with the previous embodiment of the feeler tip assembly, this structure, along with the desirable effect of the highly flexible plug filament, assists in straightening the entire kinked portion to allow passage of the source wire therethrough.

Although presently preferred and alternative embodiments and methods of assembly, use and treatment have been disclosed herein, it will be apparent to those skilled in the art that variations and modifications of these illustrative embodiments and methods may be made without departing from the true spirit and scope of the invention. It is therefore intended that the invention shall be limited only by the appended claims and the rules and principles of applicable law.

What is claimed is:

1. For use in treating malignant tumors within a patient's body by localized in vivo radiation thereof with a radioactive source, via a catheter providing a path from a point external to the body to the tumor site, the improvement comprising:

a thin, generally cylindrical, flexible elongate metal tube having a proximal end and a distal tip, a backbone wire encased within the tube from the proximal end thereof to a point short of the distal tip thereof to strengthen and enhance the flexibility of the tube, a generally cylindrical radioactive source encased and secured within the tube adjacent to the distal tip thereof in abutting relation at one end to said backbone wire, a generally cylindrical plug encased within the tube at the distal tip thereof in abutting relation to the other end of said radioactive source, said distal tip of the tube being securely and tightly enclosed about the end of said plug opposite to the end thereof in abutting relation to the radioactive source, to form a closed tip portion, said radioactive source being secured in said tube substantially solely by the pressure exerted by said tube on its cylindrical surface and the pressure exerted on its ends by said backbone wire and said plug within said closed tip portion, said tube and the backbone wire, radioactive source and plug encased therein forming a composite source wire having an overall diameter adapted to permit the source wire to be moved longitudinally through the catheter, whereby said source may be advanced into the catheter to the tumor site for radiation treatment of the tumor and thereafter withdrawn through the catheter, from said point external to the body.

2. The improvement according to claim 1, wherein said tip portion is tapered to ease the advancement of said composite source wire through said catheter 3. The improvement according to claim 1, wherein the exterior surface of said metal tube is gold plated throughout at least its length between the ends of said radioactive source encased therein.

4. The improvement according to claim 3, wherein the gold plating extends over said tip portion of said tube to preclude oxidation of the plated surface thereof and to improve the seal at said tip portion.

5. The improvement according to claim 1, wherein said metal tube is composed substantially entirely of stainless steel.

6. The improvement according to claim 1, wherein said metal tube is crimped at the tip portion thereof to assist in securing said radioactive source in place.

7. The improvement according to claim 1, wherein said radioactive source has a charge level of at least approximately one curie at the time of its encasement in said tube.

8. The improvement according to claim 7, wherein said composite source wire has a diameter of less than approximately 0.7 millimeter 9. The improvement according to claim 8, wherein said radioactive source is composed of substantially pure iridium, has a length of approximately one centimeter and a diameter of about 0.35 millimeter, and said tube has an outer diameter of less than 0.6 millimeter.

10. The improvement according to claim 7, wherein said composite source wire has a diameter of less than approximately 0.025 inch.

11. The improvement according to claim 10, wherein said radioactive source is composed of substantially pure iridium and has a length of at least approximately two centimeters, and said tube has an outer diameter of less than 0.020 inch.

12. The improvement according to claim 1, wherein said radioactive source has a radioactivity level of up to approximately 1 curie at the time of its encasement In said metal tube.

13. The improvement according to claim 12, wherein said composite source wire has a diameter of less than approximately 0.023 inch.

14. The improvement according to claim 13, wherein said radioactive source is composed of substantially pure iridium, has a diameter of about 0.005 inch and a predetermined length selected according to the size of the tumor to be treated, and said tube has an outer diameter of approximately 0.020 inch.

15. A composite radioactive source wire for radiation treatment of tumors from within, comprising:
a thin flexible elongate metal tube having proximal and distal ends and having an outer diameter adapted to permit said tube to be maneuvered through an implanted catheter to the tumor site,
a rigid radioactive core tightly secured within said tube between (i) a backbone wire secured to said tube adjacent to the distal end thereof and running substantially the entire length of said tube from the proximal end thereof, said wire having a diameter approximately equal to the inner diameter of said tube, and (ii) a plug enclosed tightly within the distal end of said tube to form a tip for said composite source wire, said core being free of welds to any of said backbone wire, said plug or said tube.

16. The invention according to claim 15, wherein said core has a radioactive strength of at least approximately one curie at the time of its assembly within the composite source wire.

17. The invention according to claim 16, wherein said composite source wire has a diameter less than approximately 0.7 millimeter.

18. The invention according to claim 17, wherein said core is composed of substantially pure iridium, has a length of approximately one centimeter and a diameter of about 0.35 millimeter, and said tube has an outer diameter of less than 0.6 millimeter.

19. The invention according to claim 16, wherein said composite source wire has a diameter of less than approximately 0.025 inch.

20. The invention according to claim 19, wherein said core is composed of substantially pure iridium and has a length of at least approximately two centimeters, and said tube has an outer diameter of less than 0.020 inch.

21. The invention according to claim 15, wherein said core has a radioactive strength of up to approximately one curie at the time of its assembly within the composite source wire.

22. The invention according to claim 21, wherein said composite source wire has a diameter of less than approximately 0.023 inch.

23. The invention according to claim 22, wherein said core is composed of substantially pure iridium, has a diameter of about 0.005 inch and a predetermined length selected according to the size of the tumor to be treated, and said tube has an outer diameter of about 0.020 inch.

24. The invention according to claim 15, wherein the exterior surface of said metal tube is plated with a noble metal over that portion of its length between said tip and the end of said core at the backbone wire.

25. The invention according to claim 24, wherein said noble metal is gold.

26. The invention according to claim 25, wherein said metal tube is stainless steel.

27. A method of treating pancreatic, liver and related organ cancers, which comprises
inserting a suitably sized catheter from a point external to the patient's body up to or through the bile duct and into the area of the organ to be treated,
inserting a closed tubular sheath of suitable size into and through the entire length of said catheter to be substantially coextensive therewith,
providing a composite source wire having a diameter less than the inner diameter of said catheter and including a radioactive core having a radioactivity strength suitable for treating the cancer, with said core secured between a backbone wire and a plug within an elongate outer tube having a distal end and a proximal end and running substantially the length of said composite source wire, said plug being affixed within the tube adjacent to the distal end thereof,
advancing said composite source wire through said catheter within the tubular sheath, including the region of or near said bile duct and the area of the organ under treatment to expose the cancerous area thereof to radiation from said core for a predetermined time interval, and
thereafter withdrawing said composite source wire from said catheter,
said tubular sheath serving to protect said composite source wire during the advancement, treatment and withdrawal.

28. The method of claim 27, including
forming said composite source wire from said tube by encasing and tightly securing therein the backbone wire of slightly smaller diameter than the tube and running virtually the entire length of the tube from the proximal end thereof to the distal end thereof except for a space large enough to accommodate said radioactive core in abutting relation to an end of said backbone wire and to the plug about which the distal end of said tube is enclosed as a tip portion for said composite source wire.

29. The method of claim 25, further including tapering said tip portion of said composite source wire to ease the advancement of said composite source wire through said tubular sheath and said catheter.

30. Apparatus for localized in vivo radiation treatment of malignant tumors, comprising
an elongate metal tube having a proximal end and a distal end,
a backbone wire having a diameter substantially equal to the inner diameter of the tube, the backbone wire being secured to the distal end of the tube and running substantially the entire length of the tube except for a portion at the distal end thereof having a length just sufficient to accommodate a radioactive core and an end plug,
said end plug spaced from said backbone wire and having a diameter similar thereto, and tightly enclosed within the tube and sealed therein at the distal end of said tube within said portion, and
a radioactive core tightly secured within said tube in abutting relation to and between the spaced confronting ends of said wire and said plug, and having a diameter similar thereto,
said tube, wire, core and plug forming a composite source wire for performing the radiation treatment.

31. The invention of claim 30, wherein the tube has a length exceeding ten centimeters and an outer diameter of less than 0.7 millimeter, and said core has a radioactive strength of at least approximately 1.0 curie.

32. The invention of claim 31, wherein said core is composed of substantially pure iridium which has been irradiated to said radioactive strength.

33. The invention of claim 30, further including a layer of material bonded to the exterior surface of the tip of said tube at the plug end thereof over the segment of its length encompassing said core, to provide a non-oxidizing region and to further seal said plug end of the tube.

34. The invention of claim 30, further including means for coupling the proximal end of the tube of said composite source wire to a drive mechanism for advancing and retracting the core to and from the tumor site.

35. For use in treating malignant tumors deep within the patient's body by localized in vivo irradiation thereof with a radioactive source, via a catheter providing a path from a point external to the body to the tumor site, the improvement comprising:
a radioactive source adapted to permit the source to be moved within the catheter,
a guidewire affixed to said source for advancing and withdrawing said source through said catheter to and from said tumor site from said point external to the body, and
tip means coupled to the source and adapted to permit straightening of said catheter at kinked portions and tight bends along said path to allow passage of said source therethrough without substantial binding.

36. The improvement according to claim 35, wherein said tip means includes a tapered head.

37. The improvement according to claim 36, wherein said tapered head includes
a relatively soft contoured tip,
a segment of soft to medium hardness behind the tip, and
a segment of medium to hard hardness behind the first-named segment.

38. The improvement according to claim 37, wherein said source is encapsulated in a flexible, nonconductive mass to preclude oxidation of the surfaces thereof.

39. The improvement according to claim 36, wherein said tapered head includes
a stack of balls secured within said tip means for freedom of rotation in respective planes normal to the axis of the head, and
one of said balls being affixed for nonrotation at the tip of said tip means.

40. The improvement according to claim 39, wherein at least some of the adjacent balls in said stack are of successively increasing diameter in the direction backward from said tip to said source.

41. A radioactive source wire for radiotherapy treatment of deep tumors, comprising:
a thin flexible elongate wire adapted to be maneuvered through a resident catheter to the tumor site,
a rigid radioactive source secured at one end to the distal end of said wire and sized for normal passage through straight regions of said catheter without binding but having a propensity for binding at tight curves in said catheter, said source having a tip opposite said one end thereof, and
feeler means secured to the tip of said source for passage through said catheter in advance of said source during advancement of said wire toward the tumor site, to straighten and open tight curves encountered by said source and thereby to ease its passage through the catheter.

* * * * *